United States Patent [19]

Acuff et al.

[11] Patent Number: 4,735,622
[45] Date of Patent: Apr. 5, 1988

[54] DISPOSABLE TRAINING PANTIES

[76] Inventors: Andila C. Acuff, HC 71 4565-1, Andrews, Tex. 79714; George Spector, 233 Broadway, Rm 3815, New York, N.Y. 10007

[21] Appl. No.: 3,647

[22] Filed: Jan. 15, 1987

[51] Int. Cl.$^4$ .............................................. A61F 13/16
[52] U.S. Cl. .............................. 604/361; 604/385 R; 604/396
[58] Field of Search ..................... 604/361, 385.1, 394, 604/395, 396, 389, 390, 391

[56] References Cited

U.S. PATENT DOCUMENTS

| | | | |
|---|---|---|---|
| 3,759,261 | 9/1973 | Wang | 604/361 |
| 4,022,211 | 5/1977 | Timmons et al. | 604/361 |
| 4,231,370 | 11/1980 | Mroz et al. | 604/361 |
| 4,615,695 | 10/1986 | Cooper | 604/394 X |
| 4,619,649 | 10/1986 | Roberts | 604/396 |

Primary Examiner—John D. Yasko

[57] ABSTRACT

A disposable training panty is provided and consists of a waterproof panty portion, an absorbent liner, an elastic waistband, elastic leg bands and a changeable happy face when wet printed thereon to help stop a child from wetting. The training panty can be opened at the crotch area so that the child can be removed from a soiled training panty. In a modification the elastic waistband is removable from the training panty so as to be used again with a new panty portion.

2 Claims, 1 Drawing Sheet

DISPOSABLE TRAINING PANTIES

BACKGROUND OF THE INVENTION

The instant invention relates generally to diapers and more specifically it relates to a disposable training panty.

Numerous diapers have been provided in prior art that are adapted to both elasticized and disposable. For example U.S. Pat. Nos. 2,544,726; 4,338,939 and 4,427,408 all are illustrative of such prior art. While these units may be suitable for the particular purpose to which they address, they would not be as suitable for the purposes of the present invention as heretofore described.

SUMMARY OF THE INVENTION

A primary object of the present invention is to provide a disposable training panty that will overcome the shortcomings of the prior art devices.

Another object is to provide a disposable training panty that will aid in potty training in which a young child can pull them up and down and the fading happy face gives the child an incentive not to wet.

An additional object is to provide a disposable training panty that can be torn away when soiled and be removed without having to be pulled down.

A further object is to provide a disposable training panty that is simple and easy to use.

A still further object is to provide a disposable training panty that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
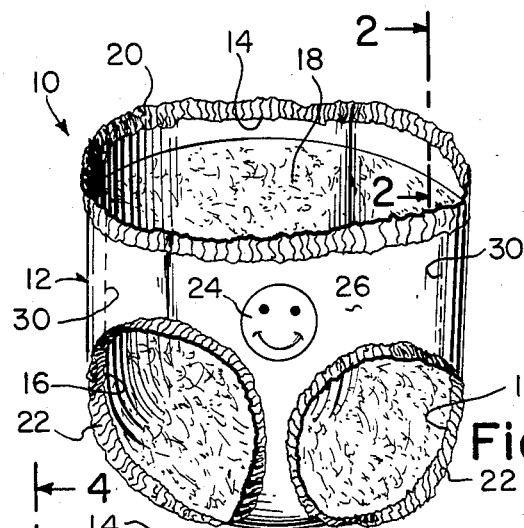
FIG. 1 is a perspective view of the invention.
Figure 2:
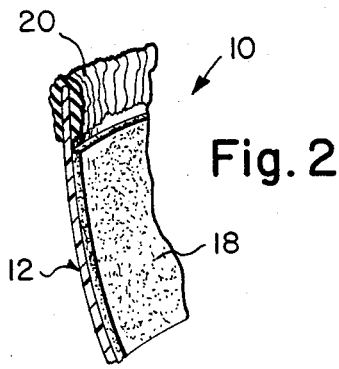
FIG. 2 is an enlarged cross sectional view taken along line 2—2 in FIG. 1.

Turning now descriptively to the drawings, in which similar reference characters denote similar elements throughout the several views, FIGS. 1 and 2 illustrate a disposable training panty 10 consisting of a panty portion 12 fabricated out of waterproof material that has a waist opening 14 and a pair of leg openings 16. A liner 18 is fabricated out of absorbent material, is generally of the same shape and secured within the panty portion 12. An elastic waistband 20 is affixed around the waist opening 14 of the panty portion 12. A pair of elastic leg bands 22 are provided, each of which is affixed around one of the leg openings 16.

Figure 6:
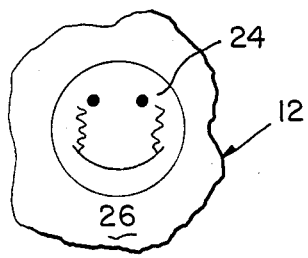
FIG. 6 is an enlarged front view of a modified face before wetting shown smiling.
Figure 7:
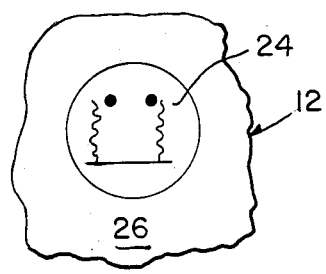
FIG. 7 is an enlarged front view of the modified face after wetting shown not smiling.
Figure 8:
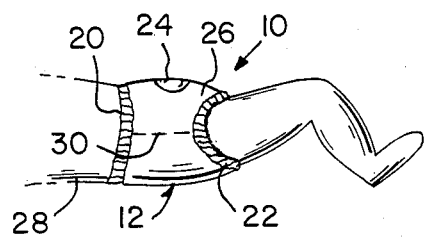
FIG. 8 is a side view of the panty intact on the child.
Figure 9:
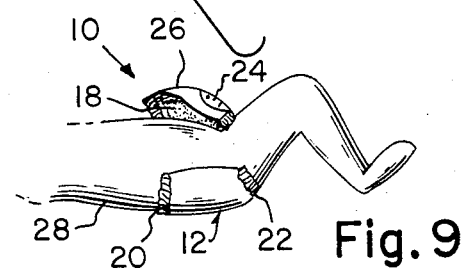
FIG. 9 is a side view of the panty being removed from the child.

A happy face 24 as best seen in FIG. 6 is printed on crotch area 26 of the panty portion 12. The happy face 24 is changeable when wet, as shown in FIG. 7, which will help stop a child wearing the training panty 10 from wetting. FIGS. 8 and 9 show that the training panty can be opened from the crotch area 26 so that the child 28 can be removed from the training panty 10 when the training panty is soiled thus keeping the child 28 clean.

A pair of perforations 30 are shown. Each extend from the elastic waistband 20 to one of the elastic leg bands 22 through the panty portion 12 and the liner 18 so that the training panty can be torn open at the crotch area 26 for easy removal of the child 28 therefrom.

Figure 3:
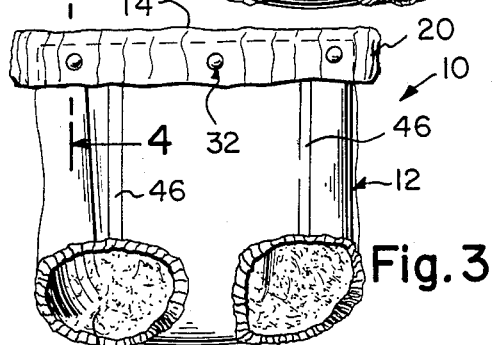
FIG. 3 is a front view of a modification in which the elastic waist band is separable from the training panty and is secured thereto by plastic pins with the panty portion having VELCRO instead of perforations for easy removal.
Figure 4:
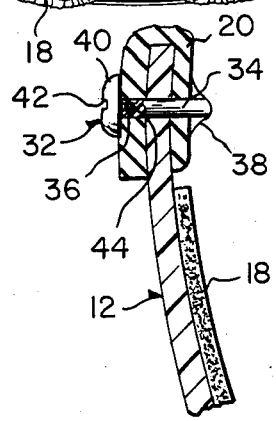
FIG. 4 is an enlarged cross sectional view taken along line 4—4 in FIG. 3.
Figure 5:
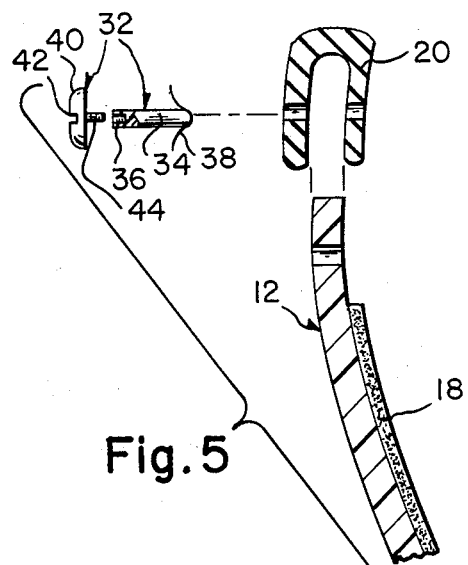
FIG. 5 is an enlarged exploded cross sectional view similar to FIG. 4 showing the plastic pin and elastic waist band separated from the panty portion.

FIGS. 3, 4 and 5 show plastic pins 32 for securing the elastic waistband 20 to the panty portion 12 at the waist opening 14 so that when the training panty 10 is soiled and must be disposed the elastic waistband 20 can be removed and used again on a new panty portion.

Each of the pins 32 consists of a shank 34 that has a threaded hole 36 at one end and a spring anchor 38 at other end. The pin 32 also includes a head 40 that has a slot 42 on one side and a threaded shaft 44 on other side. The shaft 44 can be threaded into the hole 36 of the shank 34 and the shank forced through the elastic waistband 20 and the panty portion 12 with the spring anchor 38 and the head 40 holding the elastic waistband 20 securely thereto. The head 40 is removable from the shank 34 when the elastic waistband 20 is removed from the panty portion 12.

Instead of the perforations 30 a pair of VELCRO strips 46 can be used as shown in FIG. 3. Each strip 46 extends on the panty portion 12 from the elastic waistband 20 to one of the elastic leg bands 22 so that the training panty 10 can be opened from the VELCRO strips 46 at the crotch area 26 for easy removal of the child 28 therefrom.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A disposable training panty comprising:
   (a) a panty portion fabricated out of waterproof material having a waist opening a pair of leg openings;
   (b) a liner fabricated out of absorbent material being generally of the same shape and secured within said panty portion;
   (c) an elastic waistband affixed around said waist opening of said panty portion;
   (d) a pair of elastic leg bands each of which is affixed around one of said leg openings;
   (e) a happy face printed on crotch area of said panty portion said happy face being changeable when wet which will help stop child from wearing said training panty when wet; and (f) means for opening said training panty from said crotch area so that said child can be removed from said training panty when said training panty is soiled thus keeping said child clean further comprising means for securing said elastic waistband to said panty portion at said waist opening so that when said training panty is soiled and must be disposed said elastic wasitband can be removed and used again on a new panty portion.

2. A disposable training panty as recited in claim 1, wherein said securing means includes a plurality of plastic pins, each of said pins comprises:

(a) a shank having a threaded hole at one end and a spring anchor at other end; and (b) a head having a slot on one side and a threaded shaft on other side so that said shaft can be threaded into said hole of said shank and said shank forced through said elastic waistband and said panty portion with said spring anchor and said head holding said elastic waistband securely thereto, said head is removeable from said shank when said elastic waistband is removed from said panty portion.

* * * * *